United States Patent [19]
Clausen et al.

[11] Patent Number: 5,145,482
[45] Date of Patent: * Sep. 8, 1992

[54] HAIR DYE COMPOSITIONS BASED ON 2,5-DIAMINO-6-NITROPYRIDINE DERIVATIVES

[75] Inventors: Thomas Clausen, Alsbach; Eugen Konrad, Darmstadt, both of Fed. Rep. of Germany

[73] Assignee: Wella Aktiengesellschaft, Darmstadt, Fed. Rep. of Germany

[ * ] Notice: The portion of the term of this patent subsequent to Aug. 21, 2007 has been disclaimed.

[21] Appl. No.: 512,665

[22] Filed: Apr. 20, 1990

Related U.S. Application Data

[63] Continuation of Ser. No. 348,660, Apr. 6, 1989, Pat. No. 4,950,302.

[30] Foreign Application Priority Data

Aug. 17, 1987 [DE] Fed. Rep. of Germany ....... 3727297

[51] Int. Cl.$^5$ .................... A61K 7/13; C07D 211/84; C07D 213/73
[52] U.S. Cl. ........................................... 8/409; 8/423; 8/407; 8/405; 546/307; 546/311
[58] Field of Search ................... 8/409, 423, 407, 405; 546/307, 311

[56] References Cited

U.S. PATENT DOCUMENTS 4,950,302 8/1990 Clausen et al. ..................... 8/409

FOREIGN PATENT DOCUMENTS 773043 2/1979 U.S.S.R. .

*Primary Examiner*—Paul Lieberman
*Assistant Examiner*—Bradley A. Swope
*Attorney, Agent, or Firm*—Michael J. Striker

[57] ABSTRACT

A composition for dyeing hair containing 2,5-diamino-6-nitropyridine, a solvent which is preferably water, a surfactant and at least one cosmetic additive selected from the group consisting of thickeners; care agents; perfume oils; complexing agents; oxidation hair dyes; and direct hair dyes; preservatives; a pH-adjusting member selected from the group consisting of ammonia, monoethanol amine and triethanol amine; and a polymer selected from the group consisting of chitosan derivatives, polyvinyl alcohol, polyacrylic acid, polymethacrylic acid, polyacrylonitrile, polyvinyl lactam and copolymers thereof.

11 Claims, No Drawings

HAIR DYE COMPOSITIONS BASED ON 2,5-DIAMINO-6-NITROPYRIDINE DERIVATIVES

This is a continuation of application Ser. No. 348,660, filed Apr. 6, 1989, now U.S. Pat. No. 4,950,301.

BACKGROUND OF THE INVENTION

The present invention relates to a process for producing 2,5-diamino-6-nitropyridine derivatives, their use in hair dyes and novel 2,5-diamino-6-nitropyridine derivatives.

Nitro dyes are in widespread use in hair dyes today. They are used in oxidation dyes as additives for the production of natural or modern shades. However, by combining several differently coloured nitro dyes it is also possible to produce hair dyes that are capable of dyeing the hair in natural or modern shades without the application of oxidizing agents.

Thus, for example, brown colorations having a natural effect can be produced by combining a yellow-dyeing nitro dye with a red-dyeing nitro dye and a blue-dyeing one. However, in addition, it is also possible to obtain modern brown shades, for example, with a yellow-dyeing nitro dye and a violet one. Therefore, nitro dyes that cover practically the entire colour spectrum from yellow via orange, red and violet to blue are required. In order to attain homogeneous colorations at the hairline and at the hair ends and for hair damaged in various ways, it is advantageous when these dyes originate from a group of chemical compounds having the same parent substance since similar physical properties that determine the absorptive power are then more readily attainable.

In addition, hair dyes must also satisfy many other requirements.

In toxicological and dermatological respects the nitro hair dyes must be reliable. A prerequisite for their use in oxidation hair dyes is that they remain stable in the presence of hydrogen peroxide in alkaline solution. Furthermore, a good light fastness, acid resistance and rubbing fastness are required for the hair colorations produced. Finally, it should be possible or produce the nitro dyes on an industrial scale by processes as simple as possible.

Nitro dyes are described in greater detail in the literature (see, for example J. C. Johnson, Hair Dyes, Noyes Data Corp., Park Ridge, N.J., U.S.A. 1973, page 43 to 91 and 113 to 124). Heretofore, it has been possible to produce yellow, red, violet and blue dyes only by means of differently substituted 2-nitro-p-phenylene diamines. Since doubts have recently been cast upon the physiological reliability of some of the 2-nitro-p-phenylene diamine derivatives there exists a great need for dyes which have a non-benzoid parent substance and better physiological properties at a color band width as identical as possible.

Hair dyes having a content of nitropyridine derivatives are known from the literature. Thus, for example, diamino-pyridine derivatives are generally described in DE-PS 1949750. However, only 2,3-diamino-5-nitropyridine derivatives which dye human hair bright yellow to orange and thus have only a limited color spectrum are mentioned as concrete examples.

Furthermore, agents for the oxidative dyeing of hair are described in DE-OS 3,334,030. These agents are said to contain specific diamino-nitropyridine derivatives having a general formula. However, no specific diamino-nitro-pyridine derivatives are mentioned in this publication. Since in DE-OS 3,334,030 nitro-pyridines are fundamentally applied jointly with developing components and are thus intended to react as coupling components within the scope of an oxidative hair dye system, they are selected according to their coupling property.

Unlike these nitropyridines the 2,5-diamino-6-nitropyridines described in the present application can, of course, also be applied as oxidation hair dyes. However, they do not react within the system but are applied as additional direct dyes. Therefore, the principal range of application of these dyes is the use in direct dyes of the type of shades that do not require the addition of oxidizing agents. The present 2,5-diamino-6-nitropyridine derivatives thus are not all applicable within the scope of DE-OS 3,334,030 and also have a chemical structure that differs completely from that of the nitro coupling elements described in the Examples.

The concrete Examples described in DE-OS 3,334,030, which also result in reddish shades, are based on an oxidative hair coloration and are due substantially to a self-reaction of the 2,5-diamino-pyridine used in said Examples. Furthermore, the nitro compounds described in this German publication are not resistant to reduction in the presence of dithionite.

Thus, no non-benzoid system of direct nitro hair dyes that can dye the hair in shades from orange to blue violet is known from the literature.

SUMMARY OF THE INVENTION

Therefore, it is the object of the present invention to make available a hair dye based on a system of direct non-benzoid nitro hair dyes which produces intensive hair colorations from yellow orange to blue violet and is reliable in physiological respects.

It has now been found that this aim can be achieved in an excellent manner by an agent for dyeing hair which has a content of dyes and of additives conventionally used for hair dyes. This agent is characterized in that it contains a 2,5-diamino-6-nitro-pyridine derivative having the general formula (VI)

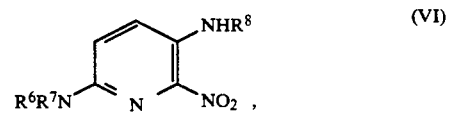

wherein $R^6$, $R^7$ and $R^8$, independently of each other, represent one of the radicals alkyl, hydroxy alkyl, dihydroxy alkyl, alkoxy alkyl, amino alkyl as well as amino alkyl substituted by alkyl or hydroxy alkyl, each alkyl radical containing 1 to 4 carbon atoms, or a heterocyclic, non-aromatic five- or six-membered ring, which can additionally contain an oxy group, is formed by $R^6$ and $R^7$, or its physiologically compatible water-soluble salt.

Among the compounds having the formula (VI) those, in which $R^6$, $R^7$ and $R^8$, independently of each other, represent hydrogen or one of the radicals methyl, ethyl or 2-hydroxy-ethyl or a pyrrolidine, piperidine of a morpholine ring is formed by $R^6$ and $R^7$, are preferred.

Very particularly suitable 2,5-diamino-6-nitro pyridine derivatives are 2,5-diamino-6-nitro-pyridine, 5-amino-((2'-hydroxyethyl)amino)-6-nitro-pyridine, 2,5-bis((2'-hydroxy-ethyl)amino)-2-N-ethyl-6-nitro-pyridine, 2,5-bis((2'-hydroxy-ethyl)amino)-6-nitro-pyridine, 2-ethyl-amino-5-((2'-hydroxy-ethyl)-amino)-6-nitro-pyridine and 5-amino-2-pyrrolidino-6-nitropyridine.

The compounds having the formula (VI), some of which are known from the literature S. Kotovskaya et at., Khim, Geterotsikl. Soedin 1981, 654 to 657 (ref. CA 95, 114439 s), .G. A. Mokrushina et a., ibid.1979, 131 (ref. CA 90, 152079 d) and from the Russian Patent 773043 and some of which are described hereafter, constitute nitro dyes that are excellently suitable for dyeing human hair. Depending on the variation of the substituents $R^6$ to $R^7$ they dye the hair yellow-orange to blue-violet. They are readily soluble in water and, particularly as component of the hair dyes according to the present invention, they have an excellent storage stability.

The very good toxicological and physiological properties of the compounds having the general formula (VI) are surprising. Thus, for example, unlike the structurally similar nitro dyes, as for example, 1,4-bis((2'-hydroxy-ethyl)amino)-2-nitro-benzene, the tested dyes, for example, the dye, wherein $R^6$ and $R^7$ represent 2-hydroxy-ethyl and $R^8$ represents hydrogen, are not mutagenic in the Ames test.

The hair dye according to the present invention relates to an embodiment in which it is applied without the addition of an oxidizing agent and also to an embodiment in which the addition of an oxidizing agent is required. The hair dye mentioned first, i.e., that without the addition of an oxidizing agent, is a dye which can also contain other conventional direct hair dyes in addition to the dye having the formula (VI). Among these dyes conventionally used for dyeing hair the following dyes are mentioned here: for example, aromatic nitro dyes, as for example, 2-amino-4-nitro-phenol, picramic acid, 1-((2'-hydroxy-ethyl)amino)-2-amino)-4-nitro-benzene, 2-nitro-4-((2'-hydroxy-ethyl)amino)aniline, 4-((2',3'-dihydroxy-propyl)amino)-3-nitro-trifluoromethyl benzene, 4-N,N'-bis((2'hydroxy-ethyl)-amino-1-methylamino-2-nitro-benzene, 2,5-bis((2'-hydroxy-ethyl)amino)-nitrobenzene, 2-((2'-hydroxy-ethyl)amino)-4,6-dinitro-phenol and 1-amino-4-((2'3'-dihydroxy-propyl)amino)-2-nitro-5-chloro-benzene; triphenyl methane dyes, as for example, Basic Violet 1 (C.I. 42 535); azo dyes, as for example, Acid Brown 4 (C.I. 14 805), anthraquinone dyes, as for example, Disperse Blue 23 (C.I. 61 545), Disperse Violet 4 (C.I. 61 105). 1,4,5,8-tetraaminoanthraquinone and 1,4-diaminoanthraquinone. Depending on the kind of their substituents the dyes of these Classes Can have an acid, nonionogenic or basic character. Further, direct hair dyes are described, for example, in the book by J. C. Johnson "Hair Dyes", Noyes Data Corp. Park-Ridge (U.S.A.) (1973), Page 3 to 91 and 113 to 139 (ISBN: 0-8155-0477-2).

The form of preparation of the described hair dyes based on direct hair dyes can be, for example, a solution, particularly an aqueous or aqueous-alcoholic solution. Furthermore, preferred forms of preparation are a cream, a gel or an emulsion. The agent can also be sprayed in mixture with a propellant or by means of a pump.

The dyes having the general formula (VI) are to be contained in this hair dye without the addition of an oxidizing agent in an amount of approximately 0.01 to 2.0 percent by weight, preferably 0.01 to 1 percent by weight. The total content of the direct hair dyes lies within the limits of approximately 0.01 to 3.0 percent by weight.

The pH value of this dye ranges from 3 to 10.5, particularly from 7.5 to 9.5. The desired alkaline pH value is adjusted primarily with ammonia but it can also be adjusted with organic amines, as for example, monoethanol amine or triethanol amine.

The dye is used in the usual manner by applying an amount of the agent to the hair that is adequate for dyeing the hair. The agent remains in contact with the hair for a period of approximately 5 to 30 minutes. Subsequently it is rinsed with water and, when required, also with the aqueous solution of a weak organic acid and then dried. For example, acetic acid, citric acid, tartaric acid and the like can be used as weak organic acid.

The above-described hair dye without the addition of an oxidizing agent can, of course, also contain synthetic or natural polymers conventionally used in cosmetics so that simultaneously with the dyeing of the hair a setting is attained. These agents are usually referred to as shade or color fixtures. Among the synthetic polymers used for this purpose in cosmetics the following synthetic polymers are mentioned here, for example, polyvinyl pyrrolidine, polyvinyl acetate, polyvinyl alcohol or polyacrylic compounds such as acrylic acid and/or methacrylic acid polymers, basic polymers of esters from these two acids and amino alcohols and/or their salts or quaternary products, polyacrylonitrile and copolymers of these compounds, as for example, polyvinyl pyrrolidonevinyl acetate and the like. Natural polymers, such as chitosan (deacetylated chitin) can also be used for this purpose.

The polymers are contained in this agent in the usual amount for these agents, i.e., approximately 1 to 5 percent by weight. The pH value of the agent ranges from approximately 6.0 to 9.0.

The application of this hair dye with additional fixation is carried out in the conventional manner by moistening the hair with the fixative, setting the hair in the desired style and by subsequently drying it.

Of course, the above-described hair dye without an added oxidizing agent can contain, when required, further additives conventionally used for hair dyes, as for example, care agents, wetting agents, thickeners, plasticizers, preservatives and perfume oils as well as conventional additives defined hereafter for oxidation hair dyes.

As mentioned at the outset, the present invention also relates to a hair dye for which the addition of an oxidizing agent is required Apart from the dyes according to the formula (VI) and, when required, conventional direct hair dyes, it also contains additional conventional oxidation hair dyes that require an oxidative development.

These oxidation hair dyes are primarily aromatic p-diamines and p-aminophenols, as for example, p-toluylene diamine, p-phenylene diamine, p-aminophenol and similar compounds which, for the purpose of varying the coloration, are combined with so-called modifiers, as for example, m-phenylene diamine, resorcinol, m-aminophenol, etc.

These oxidation dyes conventionally used for dyeing hair are described among other hair dyes in the book "Cosmetics" by E. Sagarin, Science and Technology (1957), Interscience publishers Inc., New York, Page 503 ff. and in the book "Handbuch der Kosmetika und Riechstoffe" by H. Janistyn, (1973), Page 338 ff.

With mixtures of these oxidation dyes and the dyes according to the above-defined formula (VI) natural blond and brown shades as well as modern shades can be very readily produced.

The dyes according to formula (VI) are contained in this dyeing agent with an added oxidizing agent in a concentration of approximately 0.01 to 2.0 percent by weight, preferably 0.01 to 1 percent by weight. The total amount of dyes in this dyeing agent is approximately 0.1 to 5.0 percent by weight.

Oxidation hair dyes usually are adjusted to be alkaline, preferably to pH values of 8.0 to 11.5, the adjustment being carried out particularly with ammonia. However, other organic amines, for example, monoethanol amine or triethanol amine, can also be used for this purpose. Suitable oxidizing agents for the development of the hair colorations are primarily hydrogen peroxide and its addition compounds. The preparation form of this hair dye can be the same as that of the hair dyes without the addition of an oxidizing agent. Preferably it is a cream or a gel.

Conventional additives in creams, emulsions or gels are, for example, solvents such as water, low aliphatic alcohols, for example, ethanol, propanol, isopropanol, glycerol, glycols, as for example, ethylene glycol and propylene glycol or even glycol ether, furthermore, wetting agents or emulsifiers from the classes of the anionic, cationic, amphoteric or non-ionogenic surface-active substances, as for example, fat alcohol sulphates, fat alcohol ether sulphates, alkyl sulphonates, alkyl benzene sulphates, alkyl trimethyl ammonium salts, alkyl betaines, oxethylated fat alcohols, oxethylated alkyl phenols, fatty acid alkanol amides, oxethylated fatty esters as well as thickeners, such as for example, higher fat alcohols, bentonite, starch, polyacrylic acid, cellulose derivatives, as for example, carboxymethyl cellulose, alginates, vaseline, paraffin oil and fatty acids and also care agents, as for example, lanolin derivatives, cholesterol, pantothenic acid and betaine as well as perfume oils and complexing agents. The above-mentioned components are used in the conventional amounts for these purposes, for example, the wetting agents and emulsifiers in concentrations of approximately 0.5 to 30 percent by weight while the thickeners can be contained in the preparations in an amount of approximately 0.1 to 25 percent by weight and the care agents in an amount of approximately 0.1 to 5 percent by weight.

The application of the above-mentioned preparations in which the addition of an oxidizing agent is required is carried out in a conventional manner in that prior to the treatment the hair dyes are mixed with the oxidizing agent and an amount of the mixture that is adequate for dyeing the hair, usually about 50 to 150 ml, is applied to the hair. After a reaction time adequate for dyeing the hair (normally about 10 to 45 minutes) the hair is rinsed with water, when required, subsequently rerinsed with the aqueous solution of a weak organic acid, as for example, citric acid or tartaric acid, and then dried.

With regard to the dyeing possibilities the hair dyes according to the present invention provide a broad spectrum of different color shades extending from natural colour shades to the ultramodern brilliant shades depending on the composition of the dye components and, depending on their composition, the dyeing agents are applied either in combination with hydrogen peroxide or without oxidizing agents.

The compounds having the formula (VI) cannot be produced by means of a method known from the benzene chemistry, i.e., by nitrating the 2,5-diamino-pyridine since its is oxidized during the nitration Furthermore, if this nitration were to succeed, it would have to be expected that the nitro group enters in the 3-position.

The only known process for producing 2,5-diamino-6-nitro-pyridine derivatives is described in the Russian Patent 73049 and in the publications by the same authors in Khim. Geterotsikl. Soedin 1979 (1), Page 131 and 1981 (5), Page 654 ff. However, a prerequisite therein is the production of the 3-azido-nitro-pyridine (VII), which can then be reacted with amines:

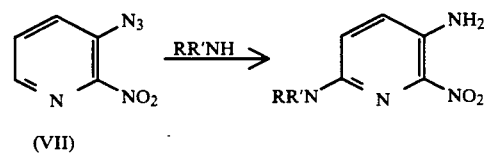

(VII)

Since the azide is thermolabile, the above production process cannot be applied on a large industrial scale.

Therefore, the present invention provides a process for producing 2,5-diamino-6-nitropyridine derivatives having the general formula (I)

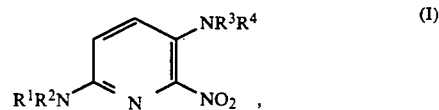

wherein, independently of each other, $R^1$ to $R^4$ represent hydrogen or one of the radicals alkyl, hydroxy alkyl, dihydroxy alkyl, alkoxy alkyl, alkoxy carbonyl, hydroxy- or chlorine-substituted alkoxy carbonyl, aminoalkyl and aminoalkyl substituted by alkyl or hydroxyl groups, the alkyl radicals in each case containing 1 to 4 carbon atoms, an oxazolidinone ring being formed by $R^1$ and $R^2$ and/or $R^3$ and $R^4$, characterized in that a 2,5-diamino-pyridine derivative having the general formula (II)

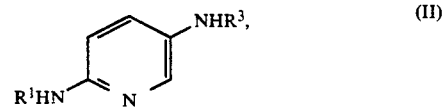

wherein $R^1$ and $R^3$ have the above-defined meaning, is reacted with a chloroformic alkyl ester to the $N^2,N^5$-bis-alkoxy-carbonyl-2,,5-diamino-pyridine derivative having the general formula (III)

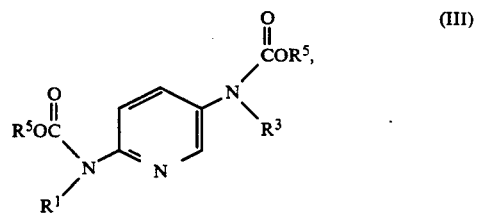

wherein $R^1$ and $R^3$ have the above-defined meaning and $R^5$ represents an alkyl or chloroalkyl radical containing 1 to 4 carbon atoms, that said derivative having the general formula (III) is then nitrated in the 6-position to the $N^2,N^5$-bis-alkoxy-carbonyl-2,5-diamino-6-nitropyridine derivative having the general formula (IV)

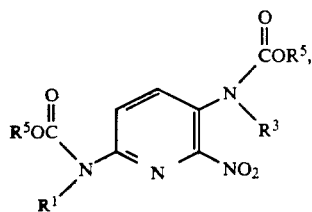

wherein $R^1$, $R^3$ and $R^5$ have the above-defined meaning, and that subsequently, if the compound having the formula (I) does not contain any alkoxy carbonyl radical, the product (IV) is converted into the 2,5-diamino-pyridine derivative having the general formula (I) by splitting off the alkoxy carbonyl radicals and by subsequent alkylation reactions known for the alkylation of aromatic amines with alkylating agents by means of which the radicals defined above for $R^3$ and $R^4$ can be introduced, for example, alkyl halides.

The fact that $N^2,N^5$-bis-alkoxy-carbonyl derivatives of the 2,5-diamino-pyridine can be nitrated without the presence of oxidation products while the nitro group enters the 6-position, although normally the position 3 that is richer in electrons is not occupied by a substituent, is a complete surprise.

Particularly favorable protective groups are the ethoxy-carbonyl group, which is inexpensive and can be readily introduced, and the 2-chloro-ethoxy-carbonyl group, which can be converted after the nitration into a 2-hydroxy ethyl group, and thus combines cleavage of the protective group and alkylation of the amino group in a single reaction step, thus extraordinarily facilitating the production of the 2-hydroxy ethyl derivatives in particular.

The novel process according to the present invention starts from the inexpensive 2,5-diamino-pyridine, that is available in industrial quantities, or its derivatives, which can be reacted to the bis-carbamate in one stage. Of course, the biscarbamates can also be obtained by rearrangement reactions from the inexpensive pyridine-2,5-dicarboxylic acid derivatives as described, for example, by H. Meyer and F. Staffen in Monatsch. Chem. 34, Page 517 ff (1913).

The novel process is particularly suitable for compounds having the formula (I), wherein the radicals $R^1$ to $R^4$, independently of each other, represent hydrogen, methyl, ethyl or 2-hydroxy ethyl or an oxazolidinone ring is formed by $R^1$ and $R^2$ and/or $R^3$ and $R^4$.

Thus, for example, as compared with the process known from the Russian Patent 773049, the production of 2,5-diamino-6-nitro-pyridine (I) ($R^1$ to $R^4$=hydrogen) is substantially facilitated by the novel process.

2,5-diamino-6-nitro-pyridine derivatives, wherein $R^1$ has the above-defined meaning but does not represent hydrogen and the radicals $R^2$, $R^3$ and $R^4$ represent hydrogen, can also be easily produced by means of the process according to the present invention. As the pattern of the formulae hereafter shows, the 2,5-diamino-6-nitro-pyridine derivatives substituted in the 2-position at the amine nitrogen and used as starting products can be obtained with advantage by nucleophilic exchange of the chlorination in the 2-chloro-5-nitropyridine:

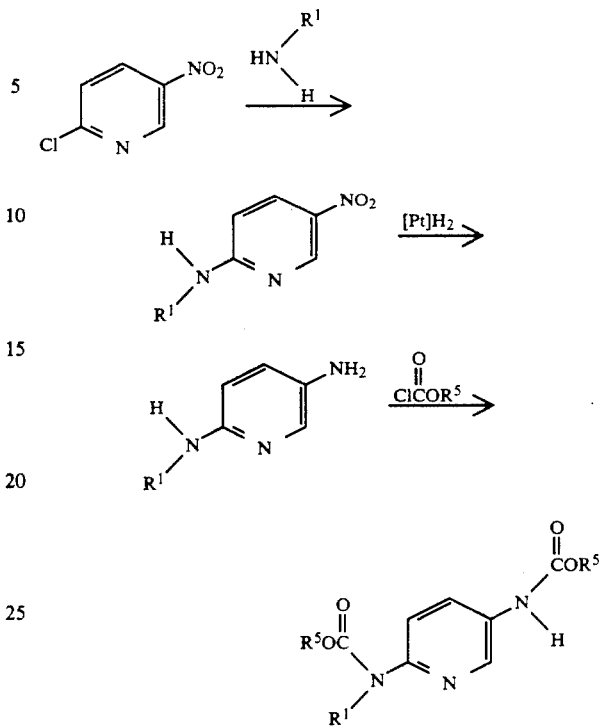

In a special embodiment of the novel process the production of hydroxy-alkylated 2,5-diamino-6-nitropyridines, for example, 2,5-bis((2'-hydroxy-ethyl)amino)-6-nitro-pyridine is made possible in that 2,5-diamino-pyridine is first reacted with chloroformic-chloro-ethyl ester to the $N^2,N^5$-bis-(2'chloro-ethoxy-carbonyl)-2,5-diamino-pyridine, the product is then nitrated in he 6-position and subsequently the 2-chloro-ethoxy-carbonyl radicals are converted by reaction with ammonia or alkyl amines, for example, ethyl amine, into oxazolidinone radicals, which are then reacted to 2-hydroxy-ethyl radicals by the action of ethanolic alkali hydroxide solution:

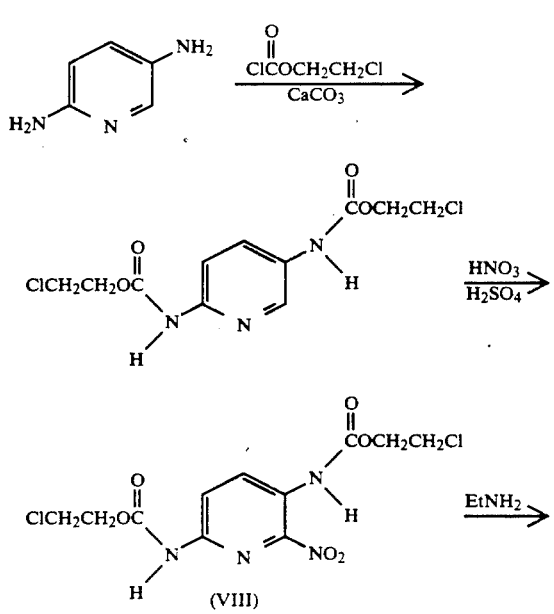

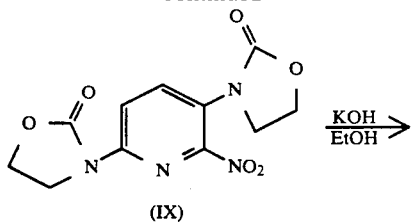

(IX)

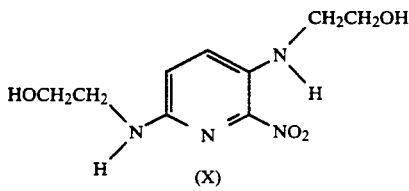

(X)

The intermediately formed bis-oxazolidinone (IX) can be isolated, but the reaction of (VIII)( to (X) can also be carried out in one step. The production of various derivatives is described in the Examples.

An entire series of 2,5-diamino-6-nitropyridine derivatives, as for example, the 2,5-bis-carbamates, the 2,5-bis-alkylamino derivatives (or the trialkyl-2,5-diamines by alkylation) is now made accessible by the novel production process.

The present invention also relates to novel 2,5-diamino-6-nitropyridine derivatives having the general formula (V)

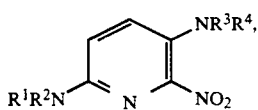

(V)

wherein $R^1$ to $R^4$ have the above-defined meaning, provided that $R^1$ to $R^4$ do not exclusively represent hydrogen and that when $R^1$ and $R^2$ represent alkyl, then $R^3$ and $R^4$ differ from hydrogen.

Examples of novel 2,5-diamino-6-nitropyridine derivatives having the general formula (V) are 2,5-bis((2'-hydroxyethyl)amino-6-nitropyridine, 2-ethyl-amino-5-((2'-hydroxyethyl)amino)-6-nitropyridine, 2,5-bis((2'-hydroxy-ethyl)amino)-2-N-ethyl-6-nitropyridine, 5-amino-2-((2'-hydroxy-ethyl)amino-6-nitropyridine and 2,5-bis(1',3'-oxazolidin-3'-yl-2'-one)-6-nitropyridine.

The novel compounds according to the present invention having the general formula (V) are yellow-orange to blue-violet direct nitro hair dyes which are extraordinarily suitable for the dyeing of human hair. They also are interesting intermediate products for the synthesis of drugs.

The following Examples illustrate the present invention.

Examples of Hair Dyes

EXAMPLE 1

Liquid Hair Dye

| | |
|---|---|
| 0.50 g | of 2,5-diamino-6-nitropyridine |
| 2.00 g | of lauryl alcohol diglycol ether sulphate-sodium salt (28 percent aqueous solution) |
| 2.00 g | of ammonia, 25 percent aqueous solution |
| 95.50 g | of water |
| 100.00 g | |

Bleached hair is treated with the solution according to Example 1 for 20 minutes at room temperature, then rinsed with water, and dried. The hair has been dyed gold-orange.

EXAMPLE 2

Dye Setting Solution

| | |
|---|---|
| 0.10 g | of 2-ethyl-amino-5-((2'-hydroxy-ethyl)amino-6-nitro-pyridine |
| 2.00 g | of polyvinyl pyrrolidone |
| 0.10 g | of glycerol |
| 40.00 g | of isopropanol |
| 57.80 g | of water |
| 100.00 g | |

White human hair is covered with the dye setting solution and dried. The hair has been dyed brilliant red-violet and set.

EXAMPLE 3

Oxidation Dye in the Form of a Cream

| | |
|---|---|
| 0.20 g | of 2,5-bis-((2'-hydroxy-ethyl)amino)-6-nitropyridine |
| 0.02 g | of 4-((2'-hydroxy-ethyl)amino)-3-nitrotoluene |
| 0.20 g | of p-phenylene diamine |
| 0.15 g | of resorcinol |
| 0.03 g | of m-aminophenol |
| 15.00 g | of cetyl alcohol |
| 3.50 g | of lauryl alcohol diglycol ether sulphate-sodium salt (28 percent aqueous solution) |
| 6.00 g | of ammonia, 25 percent aqueous solution |
| 74.90 g | of water |
| 100.00 g | |

Shortly before the application 50 g of the above hair dye are mixed with 50 ml of a 6 percent hydrogen peroxide solution. The mixture is then applied to gray human hair and allowed to react for 30 minutes at a temperature of 40° C. After rinsing the hair with water and then drying it the hair has assumed a modern red blond shade.

EXAMPLE 4

Hair Dye in the Form of a Cream

| | |
|---|---|
| 0.030 g | of 5-amino-2-pyrrolidino-6-nitropyridine |
| 0.050 g | of 4-((2',3'-dihydroxy-propyl)amino)-3-nitro-trifluoromethyl benzene |
| 0.250 g | of 4-N,N'-bis((2'-hydroxy-ethyl)amino)-1-methyl-amino-2-nitrobenzene |
| 0.025 g | of Disperse Blue 23 (C.I. 61 545) |
| 7.500 g | of cetyl alcohol |
| 1.750 g | of lauryl alcohol diglycol ether sulphate-sodium salt (28 percent aqueous solution) |
| 0.100 g | of p-hydroxy benzoic methyl ester |
| 0.200 g | of ammonia, 25 percent aqueous solution |
| 90.095 g | of water |
| 100.00 g | |

50 g of the above hair dye are applied to white human hair and after a reaction time of 20 minutes the hair is rinsed with water and then dried. It has assumed a natural brown shade.

EXAMPLE 5

Liquid Hair Dye

| | |
|---|---|
| 0.10 g | of 2,5-bis((2'-hydroxy-ethyl)amino)-2-N-ethyl-6-nitro-pyridine |
| 0.25 g | of 4-((2'hydroxy-ethyl)amino)-3-nitro-chloro-benzene |
| 0.20 g | of 4-N-ethyl-1,4-bis((2'-hydroxy-ethyl)amino)2-nitro-benzene |
| 0.50 g | of hydroxy-ethyl cellulose |
| 5.00 g | of lauryl alcohol diglycol ether sulphate-sodium salt (28% aqueous solution) |
| 10.00 g | of isopropanol |
| 10.00 g | of ammonia, 28 percent aqueous solution |
| 73.95 g | of water |
| 100.00 g | |

Bleached hair is treated with the solution according to Example 5 for 20 minutes at room temperature. After rinsing the hair with water, followed by drying, it has assumed a modern dark Beaujolais shade.

EXAMPLE 6

Liquid Hair Dye

| | |
|---|---|
| 0.05 g | of 2,5-bis((2'-hydroxy-ethyl)amino)-2-N-ethyl-6-nitro-pyridine |
| 0.30 g | of 4-((2'-ureido-ethyl)amino)-nitrobenzene |
| 5.00 g | of lauryl alcohol diglycol ether sulphate-sodium salt (28 percent aqueous solution) |
| 10.00 g | of isopropanol |
| 10.00 g | of ammonia, 25 percent aqueous solution |
| 74.65 g | of water |
| 100.00 g | |

The above hair dye is allowed to act on bleached natural hair for 30 minutes at 40° C. After rinsing the hair with water, followed by drying it has assumed a modern blond shade.

EXAMPLE 7

Hair Dye in the Form of a Cream

| | |
|---|---|
| 0.7 g | of 5-amino-2-((2'-hydroxy-ethyl)amino)-6-nitropyridine |
| 10.0 g | of cetyl stearyl alcohol |
| 5.0 g | of lauryl alcohol diglycol ether sulphate-sodium salt (28 percent aqueous solution) |
| 0.5 g | of perfume |
| 0.1 g | of sodium hydroxide |
| 83.7 g | of water |
| 100.0 g | |

The dyeing agent is allowed to act on blond natural hair for 20 minutes at 20° C. After rinsing and drying the hair has been dyed brilliant orange.

EXAMPLE 8

Hair Dye in the Form of a Cream

On replacing the 5-amino-2-((2'-hydroxy-ethyl in Example 7 by the same amount of 2,5-bis((2'-hydroxy-ethyl)amino)-6-nitro-pyridine the hair is dyed brilliant fiery red.

Production Example

EXAMPLE 9

2,5-bis(ethoxy-carbonyl-amino)-6-nitropyridine

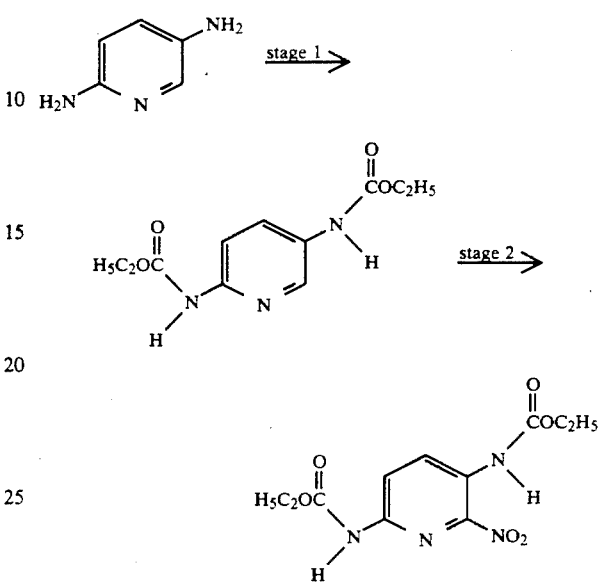

Stage 1: 2,5-bis(ethoxy-carbonyl-amino)-pyridine 10 g of 2,5-diamino-pyridine are suspended together with 20 g of calcium carbonate in 100 ml of dioxane while stirring and heated to 70° C., whereupon 20 ml of chloroformic ethyl ester are slowly added dropwise and stirring is continued over night at 70° C. Subsequently while rewashing with dioxane some of the excess calcium carbonate is filtered with suction while still hot and the filtrate is concentrated in vacuo. The residue crystallizes from ethanolic solution. The compound can also be produced according to H. Meyer and F. Staffen, Monatsch. Chemie 34, Page 517 ff. (1913).

Stage 2: 2,5-bis(ethoxy-carbonyl-amino-6-nitropyridine 40 ml of concentrated sulphuric acid are cooled to 8° C. and 5 g of the compound of Stage 1 are added while stirring. At 5° C., 5 ml of concentrated nitric acid are then added dropwise and stirring is continued for 1 hour. Subsequently the mixture is poured on 300 to 400 g of ice and the precipitated crystals are isolated by filtering with suction 4 g of a yellow crystalline compound are obtained. On recrystallizing from ethanol this compound melts at 193° C.

$^1$H-NMR Spectrum: 10.38 (s, NH), 9.72 (s, NH), 8.23 (d, J=9 Hz, 4-H), 8.10 (d, J=9 Hz, 3-H), 4.19d (q, J=7 Hz, OCH$_2$), 4.13 (q, J=7 Hz, OCH$_2$), 1.25 (t, J=7 Hz, CH$_3$), 1.23 (t, J=7 Hz, CH$_3$).

For this spectrum and all the other NMR spectra the following data apply:

All of the data in delta (p.p.m.) are relative to tetramethyl silane as standard with delta=0. Unless stated otherwise, DMSO-d$_6$ was used as solvent. s=singlet, d=doublet, t=triplet, q=quartet, m=multiplet.

Mass Spectrum: 298 (M$^+$, 65), 253 (11), 252 (32), 225 (15), 224 (100), 180 (20), 98 (M 78 (36), 154 (12), 152 (39), 134 (18), 108 (35), 107 (48), 106 (22), 96 (10), 95 (15), 81 (42), 80 (50), 79 (92), 54 (18), 53 (21), 52 (14).

For this mass spectrum and all the other mass spectra the following data apply:

All the data are in m/e (relative intensity) for all the peaks having a relative intensity greater than or equal to 10 percent.

EXAMPLE 10

2,5-diamino-6-nitropyridine

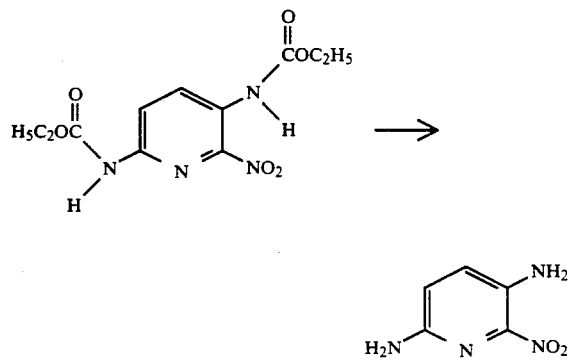

4.0 g of the biscarbamate of Example 9 are boiled in 200 ml of an ethanolic 3 percent potassium hydroxide solution for 18 hours with reflux. This is followed by filtering and the filtrate is acidified with concentrated sulphuric acid, whereupon it is concentrated in vacuo. The residue is taken up in methanol. The desired product then crystallizes as hydrochloride (melting point 241° C.).

$^1$H-NMR spectrum: 7.84 (s, broad; $NH_2$; the signal disappears on shaking the sample with $D_2O$) 7.74 (d, I=10 Hz; 4-H) 7.26 (DI=10 Hz; 3-H).

Mass Spectrum: 154 (M+, 58), 108 (47), 80 (57), 79 (20), 78 (13), 54 (72), 53 (32), 52 (20), 37 (61), 35 (100).

EXAMPLE 11

N-(5'ethoxy-carbonyl-amino-6'-nitro-pyrid-2'-yl)-N-ethoxy-carbonyl-2-amino-ethyl-ethyl carbonate

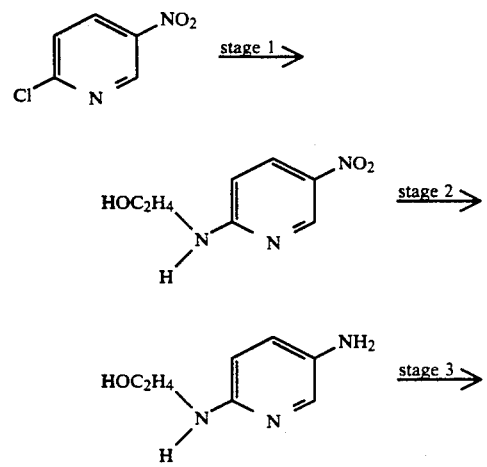

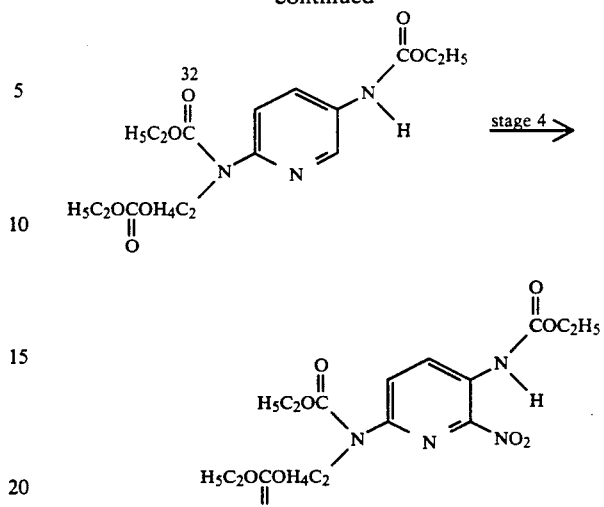

Stage 1: 2-((2'-hydroxy-ethyl)amino)-5-nitropyridine 10 g of 2-chloro-5-nitropyridine are stirred in 30 ml of ethanol amine at room temperature.

After approximately 5 minutes on exothermic reaction starts; it is completed after one hour. The mixture is poured on 200 g of ice and the yellow precipitate is isolated by filtering with suction. Upon drying 9.5 g of the amino compound are obtained.

Stage 2: 5-amino-2-((2'hydroxy-ethyl)amino)-pyridine 9.5 g of the product from Stage 1 are catalytically reduced in 200 ml of methanol on platinum with hydrogen at standard pressure and at room temperature. Upon taking up 3.7 liters of hydrogen the mixture is filtered off from the catalyst and the filtrate is concentrated in vacuo. The residue is slightly oxidized by atmospheric oxygen and therefore it is used in Stage 3 without purification. In fact the diamino hydrochloride compound is commercially available in the form of the dihydrochloride, but the free base, which can be easily produced with a good degree of purity in the manner described, is a prerequisite for successfully producing Stage 3.

Stage 3:
N-(5'-ethoxy-carbonyl-amino-pyrid-2'-yl)-N-ethoxycarbonyl-2-aminoethyl-ethylcarbonate The diamine compound of Stage 2 is dissolved in 120 ml of dioxane. After adding 12 g of calcium carbonate the solution is heated to 80° C. while stirring and 10 ml of chloroformic ethyl ester are slowly added dropwise. After stirring for 18 hours at 80° C. the mixture is filtered and the filtrate concentrated in vacuo. The dark oil obtained is applied in Stage 4 without any further purification (yield 5.0 g).

Stage 4:
N-(5'-ethoxy-carbonyl-amino-6'-nitro-pyrid-2'-yl)-N-ethoxy-carbonyl-2-aminoethyl-ethyl carbonate The nitration is carried out analogously to Example 9, Stage 2. From 5 g of the preceding Stage 2.4 g of the nitro compound are obtained.

$^1$H-NMR Spectrum 9.83 (s, NH; signal disappears on shaking the sample with $D_2O$), 8.20 (d, J=9 Hz, 4-H), 8.13 (d, J=9 Hz,3-H), 4.4-3.9 (m from 5 individual q:

OCH$_2$—and/or N—CH$_2$—), 1.27 (t, J=7 Hz, CH$_3$), 1.24 (t, J=7 Hz, CH$_3$), 1.15 (t, J=7 Hz, CH$_3$).

Mass Spectrum: 414 (M$^+$, 17), 308 (16),, 307 (100), 252 (10), 239 (16), 235 (14), 178 (21), 167 (11), 164 (17), 120 (12), 89 (20), 45 (11).

EXAMPLE 12

5-amino-2-((2'-hydroxy-ethyl)amino)-6-nitropyridine

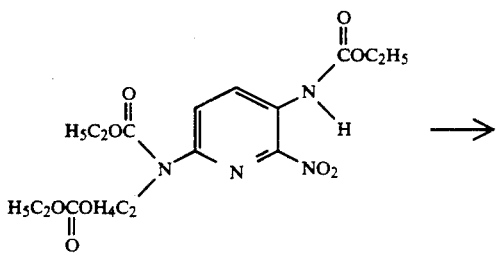

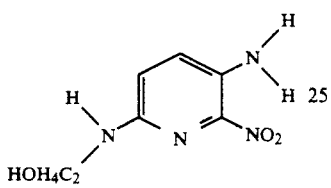

5.0 g of the tris-carbamate of Example 11 are stirred for 2½ days at room temperature in 100 ml of a 3 percent ethanolic potassium hydroxide solution. After this period the mixture is filtered and once more stirred with additional 100 ml of the potassium hydroxide solution for 2 days and filtered again. The filtrates are combined and adjusted with acetic acid to a pH of 5 to 6. The alcohol is then distilled off in vacuo and the residue is recrystallized from ethanol. 1.3 g of red crystals having a melting point of 185° C. are obtained Mass Spectrum:
198 (M$^+$, 29), 168 (10), 167 (94), 154 (14), 151 (11), 137 (12), 121 (24), 120 (72), 108 (13), 107 (21), 106 (12), 96 (11), 95 (10), 94 (31), 93 (62), 92 (29), 81 (48), 80 (62), 79 (91), 67 (33), 66 (41), 65 (17), 64 (24), 54 (100), 53 (82), 51 (75).

EXAMPLE 13

2,5-bis(2'chloro-ethoxy-carbonyl-amino)-6-nitropyridine

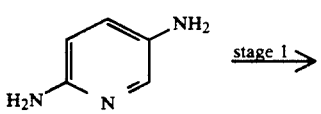

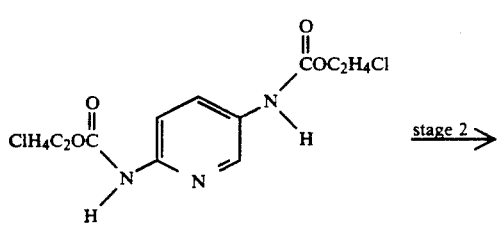

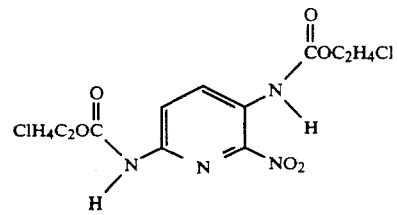

Stage 1:
2,5-bis(2'-chloro-ethoxy-carbonyl-amino)-pyridine

As described in Example 9, Stage 1, 30 g of 2,5-diamino pyridine in 200 ml of dioxane are reacted with 40 ml of chloroformic chloroethyl ester while adding 60 g of calcium carbonate. After the recrystallization 22 g of colorless crystals having a melting point of 198° C. are obtained.

Stage 2:
2,5-bis(2'chloro-ethoxy-carbonyl-amino)-6-nitropyridine

The nitration is carried out analogously to Example 9, Stage 2 (composition: 22 g of primary stage of Stage 1, 200 ml of concentrated sulphuric acid, 20 ml of concentrated nitric acid, 800 g of ice) and results in 18 g of the desired product in the form of colorless crystals having a melting point of 118° to 119° C.

Mass Spectrum: 320 (2), 318 (10), 316 (14; m/e 320, 318 and 316: M$^+$), 322 (19), 320 (29), 178 (15), 80 (10), 79 (31), 65 (30), 63 (100).

EXAMPLE 14

2,5-bis(1',3'-oxazolidin-3'-yl-2'-one)-6-nitro pyridine

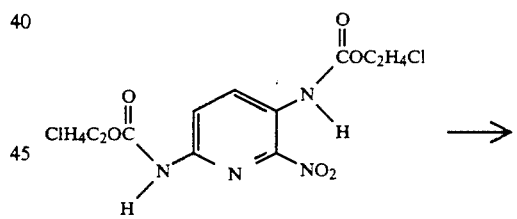

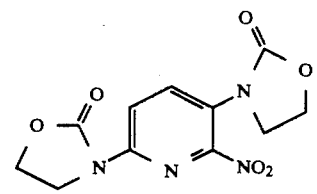

5 g of bis-carbamate of Example 9 are heated with 20 ml of a methanol solution saturated with NH$_3$ gas in an autoclave for 3 hours to 120° C. On cooling and concentrating 4.0 g of the bisoxazolidinone crystallize (melting point 22° C.).

$^1$H-NMR Spectrum: 8.46 (d, J=9 Hz, 4-H), 8.29 (d, J=9 Hz, 3-H), 4.65-4.4 (m, O—CH$_2$—), 4.27-4.02 (m. N—CH$_2$).

Mass Spectrum: 294 (15, M$^+$), 249 (12), 248 (100), 132 (15), 118 (10), 117 (21), 106 (10), 105 (33), 92 (15), 79 (29), 78 (12), 64 (22), 52 (16).

EXAMPLE 15

2,5-bis(2'-hydroxy-ethyl)amino-6-nitropyridine 5 g of the bis-oxazolidinone of Example 14 are stirred in 100 ml of a 3 percent ethanolic potassium hydroxide solution for 4 days at room temperature. Subsequently some of the precipitate is filtered with suction and the filtrate is adjusted with acetic acid to a pH value of 5 to 6. The ethanol is evaporated in vacuo and the residue is taken up in 50 ml of water. This solution is repeatedly extracted with acetic ester, the combined extracts are dried over sodium sulphate and concentrated until the crystallization begins. 2 g of the product in the form of green crystals are obtained (melting point 158° C.).

|     | Elementary Analysis | |
| --- | --- | --- |
|     | computed | obtained |
| % C | 44.65 | 44.67 |
| % H | 5.78  | 5.65  |
| % N | 23.13 | 22.98 |

$^1$H-NMR Spectrum: 7.99 (t, I=5 Hz, OH; the signal disappears when shaking the sample with $D_2O$), 7.50 (d, I=10 Hz, 4-H), 7.02 (d, I=10 Hz, 3-H), 6.58 (t I=5 Hz, OH; the signal disappears when shaking the sample with $D_2O$); 5.05-4.6 (broad, NH the signal disappears when shaking the sample with $D_2O$), 3.55 (t, I=5 Hz, broad signals; O—$CH_2$—; after shaking the signal with $D_2O$ sharper absorption) 3.45-3.20 (m, broad signals, N—$CH_2$).

Mass Spectrum: 248 (52, M+), 211 (100), 164 (10), 150 (21), 136 (14), 122 (14), 121 (24), 120 (20), 119 (13), 108 (13), 107 (15), 106 (23), 105 (15), 94 (18), 93 (38), 92 (15), 80 (19), 79 (32), 78 (15), 66 (25), 64 (15), 54 (19), 53 (15), 52 (23).

EXAMPLE 16

2,5-bis(2'-chloro-ethoxy-carbonyl amino)-2-N-ethyl-6-nitropyridine

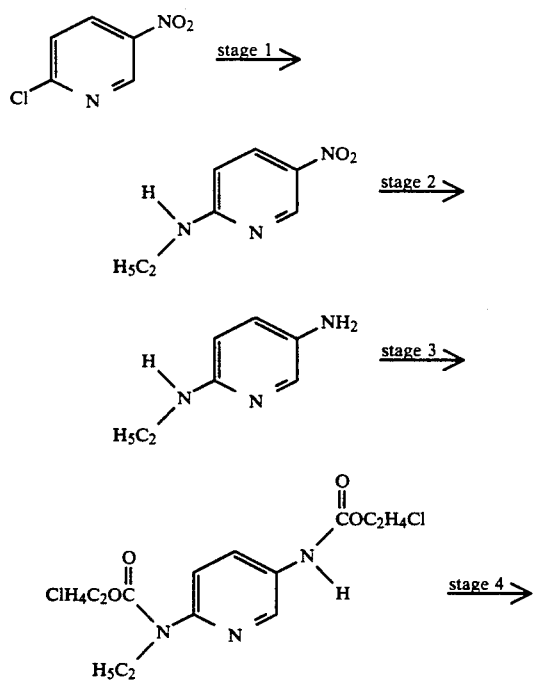

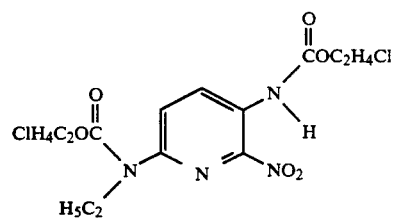

Stage 1: 2-ethyl-amino-5-nitro-pyridine 10 g of 2-chloro-5-nitropyridine are mixed with 30 ml of ethyl amine. After a few minutes an exothermic reaction starts. On its completion stirring is continued for 30 minutes. The mixture is poured on 150 g of ice and filtered with suction from the precipitated crystals. On recrystallizing from ethanol 9.6 g of yellow crystals having a melting point of 118° C. are obtained.

$^1$H-NMR Spectrum (in $CDCl_3$): 9.01 (d, J=3 Hz, 6-H), 8.18 (dd, $J_1$=3 Hz, $J_2$=10 Hz, 4-H), 6.37 (d, $J_2$=10 Hz, 3-H), 5.5 (broad, NH), 3.46 (dq, $J_1$=6 Hz, NH-coupling; $J_2$=7 Hz, $CH_2$), 1.31 (t, J=7 Hz, —$CH_3$).

Stage 2: 5-amino-2-ethyl-amino-pyridine 9 g of the nitro compound of Stage 1 are hydrogenated in methanol on platinum with hydrogen at standard pressure and at room temperature. On taking up the theoretical amount of hydrogen the mixture is filtered off from the catalyst and concentrated. The residue (6.8 g) is used in Stage 3 without further purification.

Stage 3: 2,5-bis(2'-chloro-ethoxy-carbonyl-amino)-2-N-ethyl-pyridine 6.8 g of the diamino compound of Stage 2 are dissolved in 30 ml of dioxane, mixed with 7.0 g of calcium carbonate, whereupon 10.6 g of chloroformic chloro ethyl ester are added dropwise while stirring at 80° C. The solution is stirred for 3 hours at this temperature and is then filtered with suction from the residue. The filtrate is concentrated in vacuo. The residue is chromatographed on silica gel (eluant: methylene chloride with 5% of methanol) and after the crystallization from water it yields 3.4 g of colorless crystals.

$^1$H-NMR Spectrum (in $CDCl_3$): 8.35 (d, $J_1$=3 Hz, 6-H), 7.87 (dd, $J_1$=3 Hz, $J_2$=9 Hz, 4-H), 7.53 (d, J=9 Hz, 3-H), 6.95 (broad, NH, when shaking the sample with $D_2O$ the signal disappears), 4.58-4.32 (m, O—$CH_2$); 3.98 (q, J=7 Hz, N—$CH_2$), 3.84-3.60 (m, Cl—$CH_2$), 1.21 (t, J=7 Hz, $CH_3$).

Mass Spectrum: 353 (3), 351 (18), 349 (28; m/e 353, 351, 349: M+), 314 (10), 244 (32), 243 (17), 242 (100), 241 (11), 206 (18), 152 (50), 93 (10), 79 (16), 55 (19), 53 (65).

Stage 4: 2,5-bis(2'-chloro-ethoxy-carbonyl-amino)-2-N-ethyl-6-nitropyridine

The nitration of 2.5 g of the compound of Stage 3 with 2.5 ml of concentrated nitric acid in 10 ml of concentrated sulphuric acid analogously to Example 9, Stage 2 results in 2 g of the nitro compound having a melting point of 87° C.

$^1$H-NMR Spectrum (in CDCl$_3$): 9.55 (broad, NH), 8.94 (d, J=9 Hz, 4-H), 8.21 (d, J=9 Hz, 3-H), 4.48 (2x t, J=6 Hz, OCH$_2$), 4.11 (q, J=7 Hz, N—CH$_2$), 3.76 (2x t, J=6 Hz, CH$_2$Cl), 1.31 (t, J=Hz, CH$_3$)

Mass Spectrum: 398 (2), 396 (10), 394 (15; m/e 398, 396, 394: M+), 377 (9), 240 (10), 178 (22), 80 (35), 65 (30), 63 (100).

EXAMPLE 17

2-ethyl-amino-5-((2'-hydroxy-ethyl)amino-6-nitropyridine 1.3 g of the bis-carbamate of Example 10, Stage 4 are suspended in 20 ml of a 5 percent potassium hydroxide solution and stirred for 2½ days at room temperature. Subsequently the reaction mixture is adjusted with glacial acetic acid to a pH value of 3 to 4 and repeatedly extracted with acetic ester. The combined extracts are dried over sodium sulphate and concentrated in vacuo. After crystallization from ethanol 0.23 g of the compound are obtained in the form of green crystals.

$^1$H-NMR Spectrum: 7.94 (t, I=5 Hz, OH or NH, signal disappears when shaking the sample with D$_2$O), 7.50 (d, I=10 Hz, 4-H), 6.94 (d, I=10 Hz, 3-H), 6.48 (t, I=5 Hz, OH or NH, signal disappears when shaking the sample with D$_2$O), 4.88 (t, I=5 Hz, OH or NH, signal disappears when shaking the sample with D$_2$O), 3.58 (t, I=5 Hz, CH$_2$OH), 3.49-3.05 (m, N—OCH$_2$), 1.14 (t, I=7 Hz, CH$_3$).

EXAMPLE 18

5-((2'-hydroxy-ethoxy-carbonyl-amino)-2-methyl-amino-6-nitropyridine

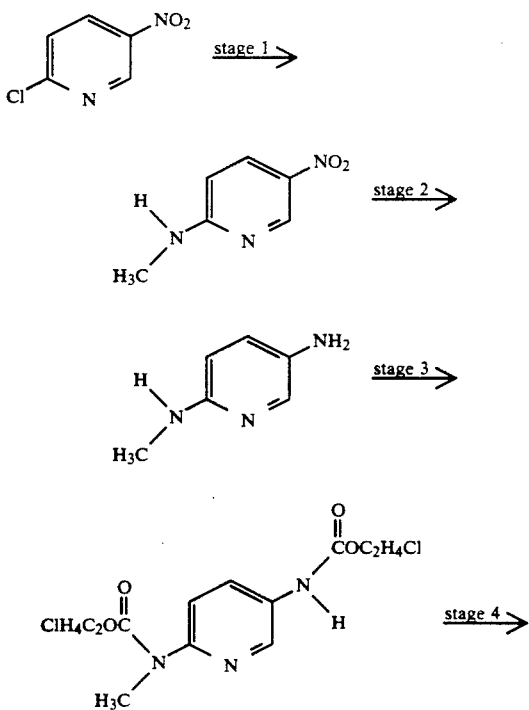

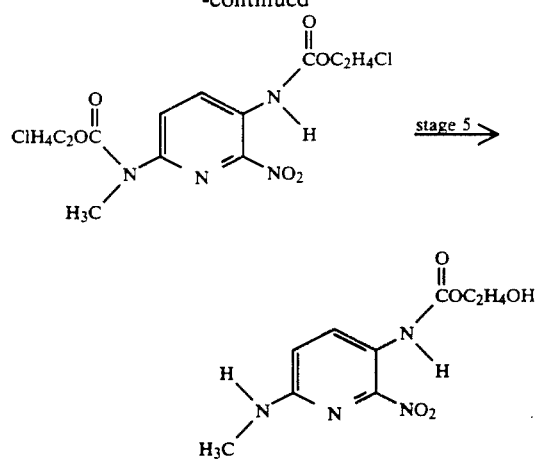

When carrying out the entire reaction sequence analogously to Example 16 (a 40 percent methyl amine solution instead of ethyl amine) and Example 17, then 5-((2'-hydroxy-ethyl)amino)2-methyl amino-6-nitropyridine is obtained in the form of green crystals.

| | Elementary Analysis | |
| --- | --- | --- |
| | computed | obtained |
| % C | 45.28 | 45.18 |
| % H | 5.69 | 5.40 |
| % N | 26.40 | 26.15 |

EXAMPLE 19

2,5-bis((2'-hydroxy-ethyl)amino-2-N-ethyl-6-nitropyridine

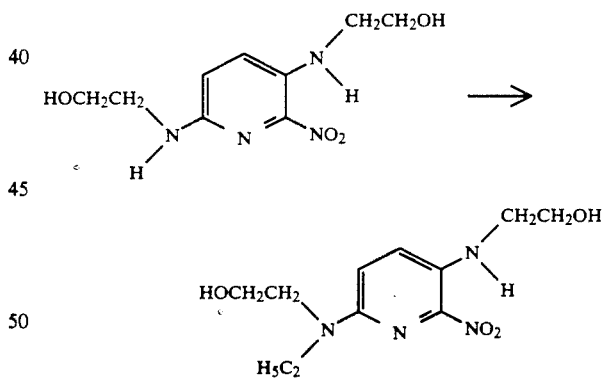

2.0 g of the bis (hydroxy-ethyl-amino)compound of Example 15 are dissolved in 50 ml of dioxane and mixed with 5 ml of ethyl iodide. On adding 5 ml of triethanol amine the mixture is stirred for 24 hours at room temperature. The mixture is then diluted with water, adjusted with acetic acid to a pH value of 5 and extracted with acetic ester. The combined extracts are dried over sodium sulphate. The solvent is then evaporated in vacuo and the residue is chromatographed on silica gel (eluant:methylene chloride with 10 percent of methanol). Green crystals of the desired compound are obtained in a low yield.

$^1$H-NMR Spectrum: 8.05 (t, I=5 Hz, OH or NH, signal disappears when shaking the sample with D$_2$O), 7.48 (d, I=9 Hz, 4-H), 6.90 (d, I=9 Hz, 3-H), 6.58 (t, I=5 Hz, OH or NH, signal disappears when shaking the sample with D₂O), 5.90 (broad, NH or OH, signal disappears when shaking the sample with D₂O), 3.7–3.1 (m, —CH₂—OH and NHCH₂—), 1.12 (t, I=7 Hz, CH₃).

The data in percent in this application refer to percent by weight unless stated otherwise.

While the invention has been illustrated and described as embodied in new 2,5-diamine-6-nitropyridine derivatives and hair dye compositions based on same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A composition for dyeing hair consisting essentially of a 2,5-diamino-6-nitropyridine derivative having the formula (VI):

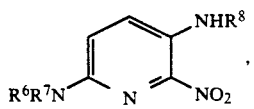

(VI)

or a physiologically compatible water-soluble salt thereof, wherein, independently of each other, $R^6$, $R^7$ and $R^8$, are selected from the group consisting of hydrogen and alkyl radicals containing one to four carbon atoms, provided at least two of $R^6$, $R^7$ and $R^8$ are hydrogen at least one solvent, at least one surfactant selected from the group consisting of anionic, cationic, amphoteric and nonionogenic surfactants and at least one cosmetic additive selected from the group consisting of thickeners, care agents, perfume oils, complexing agents, oxidation hair dyes, additional direct hair dyes, perservatives, a pH-adjusting member selected from the group consisting of ammonia, monoethanol amine and triethanol amine; and a polymer selected form the group consisting of chitosan, chitosan derivatives, polyvinyl alcohol, polyacrylic acid, polymethacrylic acid, polyacrylonitrile, polyvinyl lactam and copolymers thereof.

2. A composition as in claim 1, wherein the 2,5-diamino-6-nitropyridine derivative having the formula (VI) is 2,5-diamino-6-nitropyridine.

3. A composition as in claim 1, wherein the 2,5-diamino-6-nitropyridine derivative having the formula (VI) is contained in an amount of 0.01 to 2.0 percent by weight.

4. A composition as in claim 1, wherein said cosmetic additive comprises said additional direct hair dye.

5. A composition as in claim 4, wherein the conventional direct hair dye is selected from the group consisting of 2-amino-4-nitro-phenol, picramic acid, 1-((2'-hydroxy-ethyl)amino-2-amino-4-nitro-benzene, 2-nitro-4-((2'-hydroxy-ethoxy)-amino-aniline, 4-((2',3'-dihydroxypropyl)amino-3-nitro-trifluoromethyl benzene, 4-N,N'-bis((2'-hydroxyl-ethyl)amino)-1-methyl-amino-2-nitro-benzene, 2,5-bis-((2'-hydroxy-ethyl)amino)-nitro-benzene, 2-((2'-hydroxy-ethyl)amino)-4,6-dinitro-phenol, 1-amino-4-((2',3'-dihydroxypropyl)amino)-2-nitro-5-chloro-benzene, Basic Violet 1 (C.I. 42 535), Acid Brown 4 (C.I. 14 805), Disperse Violet 4 (C.I. 61 105), Disperse Blue 23 (C.I. 61 545), 1,4,5,8-tetraamino anthraquinone and 1,4-diamino anthraquinone.

6. A composition as in claim 4, wherein said cosmetic additive comprises said polymer.

7. A composition as in claim 1, wherein said cosmetic additive comprises one of the oxidation hair dyes.

8. A composition as in claim 7, wherein the oxidation hair dye is selected from the group consisting of p-toluylene diamine, p-phenylene diamine, p-aminophenol, m-phenylene diamine, resorcinol and m-aminophenol.

9. A composition for dyeing hair consisting essentially of 0.01 to 2% by weight of a 2,5-diamino-6-nitropyridine, at least one solvent, at least one surfactant selected from the group consisting of anionic, cationic, amphoteric and nonionogenic surfactants and at least one cosmetic additive selected from the group consisting of thickeners, care agents, perfume oils, complexing agents, oxidation hair dyes, additional direct hair dyes, preservatives, a pH-adjusting member selected from the group consisting of ammonia, monoethanol amine and triethanol amine; and a polymer selected from the group consisting of chitosan, chitosan derivatives, polyvinyl alcohol, polyacrylic acid, polymethacrylic acid, polyacrylonitrile, polyvinyl lactam and copolymers thereof.

10. A composition as defined in claim 9, wherein said surfactant is lauryl alcohol diglycol ether sulphate-sodium salt.

11. A composition as defined in claim 9, wherein said solvent is water and said cosmetic additive is ammonia.

* * * * *